(12) United States Patent
Zhang et al.

(10) Patent No.: US 11,585,779 B2
(45) Date of Patent: Feb. 21, 2023

(54) BIOSENSOR AND METHOD OF USING THE SAME FOR EVALUATION OF ANTIOXIDANT CAPACITY

(71) Applicant: Nanjing Agricultural University, Nanjing (CN)

(72) Inventors: Wangang Zhang, Nanjing (CN); Qingfeng Ge, Nanjing (CN); Donglei Jiang, Nanjing (CN); Panwei Ge, Nanjing (CN); Guanghong Zhou, Nanjing (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 642 days.

(21) Appl. No.: 16/689,034

(22) Filed: Nov. 19, 2019

(65) Prior Publication Data
US 2020/0103365 A1 Apr. 2, 2020

Related U.S. Application Data

(63) Continuation-in-part of application No. PCT/CN2018/095696, filed on Jul. 13, 2018.

(30) Foreign Application Priority Data

Aug. 14, 2017 (CN) .................. 201710689718.X (51) Int. Cl.
| | | |
|---|---|---|
| G01N 27/327 | (2006.01) | |
| C12Q 1/02 | (2006.01) | |
| G01N 27/60 | (2006.01) | |
| G01N 33/50 | (2006.01) | |
| G01N 27/416 | (2006.01) | |

(52) U.S. Cl.
CPC ........ *G01N 27/3278* (2013.01); *C12Q 1/025* (2013.01); *G01N 27/3272* (2013.01); *G01N 27/4166* (2013.01); *G01N 27/60* (2013.01); *G01N 33/5055* (2013.01); *G01N 27/3275* (2013.01); *G01N 2500/10* (2013.01); *G01N 2800/7009* (2013.01)

(58) Field of Classification Search
CPC .......... G01N 27/3278; G01N 27/3272; G01N 27/4166; G01N 27/60; G01N 27/3275; G01N 33/5055; G01N 2500/10; G01N 2800/7009; C12Q 1/025
See application file for complete search history.

(56) References Cited

PUBLICATIONS

Reybier, Karine et al. (2010) Characterization of oxidative stress in Leishmaniasis-infected or LPS-stimulated macrophages using electrochemical impedance spectroscopy. Biosensors and Bioelectronics, vol. 25 (n° 12) pp. 2566-2572 (Year: 2010).*

Yan et al., Electrochemical biosensors for on-chip detection of oxidative stress from immune cells, Biomicrofluidics 5, 032008 (2011) (Year: 2011).*

* cited by examiner

*Primary Examiner* — Alexander S Noguerola
(74) *Attorney, Agent, or Firm* — Matthias Scholl P.C.; Matthias Scholl (57) ABSTRACT

A biosensor, including a modified gold electrode and a macrophage RAW264.7 immobilized on the modified gold electrode. The disclosure also provides a method of preparing the biosensor and a method of using the same for evaluation of antioxidant capacity of substances.

8 Claims, 7 Drawing Sheets

BIOSENSOR AND METHOD OF USING THE SAME FOR EVALUATION OF ANTIOXIDANT CAPACITY

CROSS-REFERENCE TO RELAYED APPLICATIONS

This application is a continuation-in-part of International Patent Application No. PCT/CN2018/095696 with an international filing date of Jul. 13, 2018, designating the United States, now pending, and further claims foreign priority benefits to Chinese Patent Application No. 201710689718.X filed Aug. 14, 2017. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to the field of evaluation of antioxidant capacity, and more particularly to a biosensor and a method of using the same for evaluation of antioxidant capacity.

Biosensors (CBBs), which employ living cells as sensing elements, can detect the functional information of biologically active analytes. Typically, CBBs are composed of biomolecule recognition elements and a physical or chemical transducer.

Oxidative stress in vivo is involved in inducing the occurrence and development of many chronic diseases. Thus, the evaluation of the antioxidant capacity of substances is of importance for the development of drugs for the prevention and treatment of diseases caused by oxidative stress. Conventional antioxidant evaluations are performed in vitro using chemicals, which fails to stimulate the antioxidant reaction mechanisms in vivo.

SUMMARY

The disclosure provides a biosensor, a preparation method thereof, and a method for evaluating antioxidant capacity using the biosensor. Specifically, the biosensor uses a macrophage as a sensing element and uses electrochemical impedance as an index to evaluate the antioxidant capacity of substances.

The disclosure provides a biosensor comprising a modified gold electrode and a macrophage RAW264.7 immobilized on the modified gold electrode.

A method for preparing a biosensor, the method comprising:
  a) dissolving manganese dioxide ($MnO_2$) in a mixed acid of concentrated $H_2SO_4$ and concentrated $HNO_3$ in an ultrasonic bath to obtain a mixed solution, stirring the mixed solution in an ice bath for 3-5 hrs, centrifuging the mixed solution, washing a resulting product with water and drying to obtain an acidified $MnO_2$ nanomaterial;
  b) dispersing the acidified $MnO_2$ nanomaterial in a chitosan solution in the presence of ultrasonic wave to obtain a suspension having a solid phase concentration of 0.9-1.1 mg/mL, taking 8-12 µL of the suspension and adding dropwise to a surface of a dried gold electrode, drying at 4-6° C., to yield a modified electrode;
  c) mixing graphene oxide and Dulbecco's Modified Eagle Medium (DMEM) having a concentration of 10 mmol/L according to a mass/volume ratio of 0.1 g/100 mL, sonicating for 4-6 min to yield a graphene oxide mixed solution, dropwise adding the graphene oxide mixed solution to a DMEM containing 1% sodium alginate, to yield a mixed gel of sodium alginate and graphene oxide, wherein the added graphene oxide mixed solution accounts for 10 wt. % of the DMEM containing 1% sodium alginate;
  d) culturing a macrophage in DMEM containing 10% (v/v) fetal bovine serum (FBS) at 37° C. in the presence of 5% (v/v) $CO_2$ for 2-3 days, to obtain a macrophage suspension; and
  e) mixing the macrophage suspension and the mixed gel of sodium alginate and graphene oxide in a volume ratio of 1:1, taking 4-6 µL of a resulting mixture and adding to a surface of the modified electrode; immersing the modified electrode in a $CaCl_2$ solution for 3-5 min, and placing the $CaCl_2$ solution in an incubator having 5% (v/v) CO2 at 37° C. for 2-4 min, to yield a biosensor.

The method can further comprise immersing the biosensor prepared in e) in Piranha solution comprising sulfuric acid and 30% hydrogen peroxide (v: v=7: 3) for 12-18 min, polishing the surface of the modified electrode into a mirror surface with $Al_2O_3$ polishing powders having particle sizes of 0.3 µm and 0.05 µm, respectively; ultrasonically washing the biosensor with 5% dilute sulfuric acid, absolute ethanol and water in sequence for 5-8 min, respectively, drying under a nitrogen atmosphere, and storing at 4° C.

The volume ratio of the concentrated $H_2SO_4$ to the concentrated $HNO_3$ in a) can be 3:1.

A method for evaluating antioxidant capacity using a biosensor, the method comprising:
  1) immersing a first biosensor in a Tyrode's buffer at 37° C., adding propylene glycol monomethyl ether acetate (PMA, 1-methoxy-2-propanol acetate) to the Tyrode's buffer until the final PMA concentration reaches 100 ng/mL, 10 min later, washing the first biosensor with PBS buffer 2-4 times, and connecting the first biosensor to a first electrochemical workstation;
  2) immersing a test sample and a second biosensor in Tyrode's buffer at 37° C., adding propylene glycol monomethyl ether acetate (PMA, 1-methoxy-2-propanol acetate) to the Tyrode's buffer until the final PMA concentration reaches 100 ng/mL, 10 min later, washing the second biosensor with PBS buffer 2-4 times, and connecting the second biosensor to a second electrochemical workstation;
  3) conducting electrochemical experiments of the first biosensor and the second biosensor in a solution containing 1.0 mM $Fe(CN)_6^{3-}$, 1.0 mM $Fe(CN)_6^{4-}$ or 0.1 M PBS, recording the current signal, reading the peak current and marking as $I_0$ and $I_s$, respectively;
  4) determining whether the test sample has antioxidant capacity:
    4.1) $I_0 > I_s$ indicates that the test sample has an antioxidant capacity, and proceeding to 5) to determine its antioxidant capacity; and
    4.2) $I_0 \leq I_s$ indicates that the test sample has no antioxidant capacity; and
  5) calculating the relative antioxidant capacity (RAC) value to evaluate the antioxidant capacity of the test sample.

The pH of the PBS buffer in 1) can be 7.4.

The electrochemical experiments in 3) can be a differential pulse voltammetry (DPV), and the DPV conditions can be as follows: scanning range: -0.2 to 0.6 V, amplitude: 0.05 V.

The relative antioxidant capacity value in 5) can be calculated by the following equation:

$$RAC = \frac{(I_0 - I_s)}{(I_0 - I)} \times 100\%$$

where RAC is the relative antioxidant capacity value, $I_0$ is the peak current obtained in the presence of 100 ng/mL PMA, $I_s$ is the peak current in the presence of the test sample, and I is the peak current in the absence of PMA.

The antioxidant capacity of the test sample in 5) can be evaluated as follows:

a value of RAC greater than 10% and less than 40% indicates that the test sample has weak antioxidant capacity;

a value of RAC between 40% and 70% indicates that the test sample has moderate antioxidant capacity; and a value of RAC greater than 70% indicates that the test sample has strong antioxidant capacity.

The method for determining the peak current I in the absence of PMA is as follows:

immersing a third biosensor in Tyrode's buffer at 37° C. for 10 min, washing the third biosensor with PBS buffer for 3 times, connecting the third biosensor to a third electrochemical workstation, and conducting an electrochemical experiment of the third biosensor in a solution containing 1.0 mM $Fe(CN)_6^{3-}$, 1.0 mM $Fe(CN)_6^{4-}$ or 0.1 M PBS, recording the current signal, reading the peak current and marking as I.

Advantages of the biosensor and the method of using the same for evaluation of antioxidant capacity according to embodiments of the disclosure are summarized as follows:

1. The biosensor uses a macrophage as a sensing element. The macrophage RAW264.7 has a relatively short culture period and low cost compared to conventional sensing elements.
2. The macrophage as a sensing element can simulate the antioxidant mechanism of living organisms.
3. The macrophages are immobilized on the gold electrode and are covered by hydrogel. This improves the adhesion of the cells on the electrode, and prolongs the service life of the cells.
4. The differential pulse voltammetry as the signal detection method is sensitive and efficient.

BRIEF DESCRIPTION OF DRAWINGS

In FIGS. 2 and 3, a is a modified gold electrode, b is an acidified manganese dioxide/gold electrode, c is a graphene oxide/sodium alginate/acidified manganese dioxide/gold electrode, and d is a biosensor;

In FIG. 5, a is a positive control, and b, c, d, e, f, and g represent Lactobacillus plantarum NJAU-01 having a concentration of $10^5$, $10^6$, $10^7$, $10^8$, $10^9$, $10^{10}$ CFU/mL, respectively.

DETAILED DESCRIPTION

To further illustrate, embodiments detailing a biosensor and a method of using the same for evaluation of antioxidant capacity are described below. It should be noted that the following embodiments are intended to describe and not to limit the disclosure.

Figure 1:
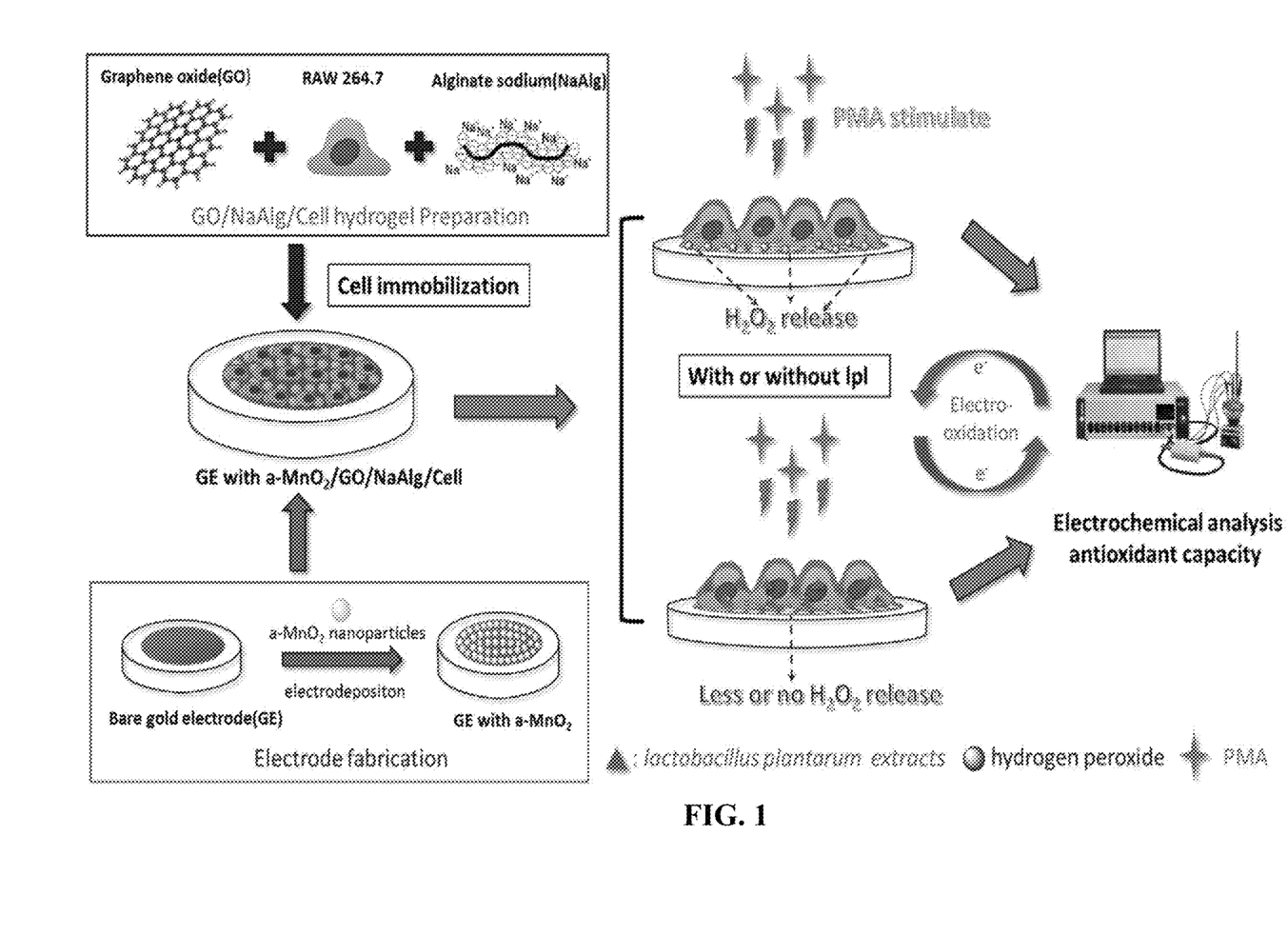
FIG. 1 is a flow chart of preparing a biosensor according to one embodiment of the disclosure.

The biosensor comprises a modified gold electrode and a macrophage RAW264.7 immobilized on the modified gold electrode, and the preparation thereof is as shown in FIG. 1.

a) Preparation of acidified manganese dioxide: dissolving manganese dioxide ($MnO_2$) in a mixed acid of concentrated $H_2SO_4$ and concentrated $HNO_3$ (the mass fraction of concentrated sulfuric acid is ≥70%, and the mass fraction of concentrated nitric acid is about 68%) in an ultrasonic bath (ultrasonic conditions: 100 kHz, time: 5min) to obtain a mixed solution, and then stirring the mixed solution in an ice bath (0° C.) for 3-5 hrs, centrifuging the mixed solution, washing a resulting product with water and drying to obtain an acidified $MnO_2$ nanomaterial.

b) Preparation of modified electrode: dispersing the acidified $MnO_2$ nanomaterial in a chitosan solution in the presence of ultrasonic wave (ultrasonic conditions: 100 KHz, time: 8 min) to obtain a suspension having a solid phase concentration of 0.9-1.1 mg/mL, taking 8-12 μL of the suspension and adding dropwise to a surface of a dried gold electrode, drying at 4-6° C., to yield a modified electrode.

c) Preparation of mixed gel: mixing graphene oxide with DMEM (glucose content is 4.5g/mL) with a concentration of 10 mmol/L at a mass/volume ratio of 0.1 g/100 mL, and sonicating (condition: 100KHz) for 4-6 min, so that the graphene oxide is uniformly dispersed in high-sugar DMEM and thus obtain a mixture of graphene oxide; dropwise adding the graphene oxide mixed solution to a DMEM containing 1% sodium alginate, to yield a mixed gel of sodium alginate and graphene oxide, wherein the added graphene oxide mixed solution accounts for 10 wt. % of the DMEM containing 1% sodium alginate.

d) Culture of macrophages: culturing the macrophages (the number of cells is controlled at $1 \times 10^7$ cells/mL) in 1×DMEM (glucose content is 4.5 g/mL) containing 10% fetal bovine serum (FBS) at 37° C. in the presence of 5% (v/v) $CO_2$ (volume fraction) for 2-3 days, to obtain a macrophage suspension.

e) Cell fixation: mixing the cell suspension and the mixed gel in a volume ratio of 1:1 (add 0.5 mL of cell suspension to 0.5 mL of mixed gel). Subsequently, taking 4-6 μL of the cell-mixed gel and adding it to the surface of the modified electrode; immersing the modified electrode in a $CaCl_2$ solution (concentration is 80-120 mM (mM means mmol/L)) for 3-5 min, and placing the $CaCl_2$ solution in an incubator having 5% $CO_2$ at 37° C. for 2-4 min, to yield a biosensor.

f) Cleaning: immersing the biosensor prepared in e) in Piranha solution (the piranha solution, also known as the piranha etchant, is a mixture of concentrated sulfuric acid and 30% $H_2O_2$ (v/v =7: 3)) for 12-18 min, and polishing the surface of the electrode into a mirror surface with $Al_2O_3$ polishing powders having particle sizes of 0.3 μm and 0.05 μm, respectively; ultrasonically (100 kHz) washing the biosensor with 5% dilute sulfuric acid, absolute ethanol and water in sequence for 5-8 min, respectively, drying under a nitrogen atmosphere, and storing at 4° C.

Electrochemical experiments of various electrodes and the biosensor in a solution containing 1.0 mM $Fe(CN)_6^{3-}$ or 1.0 mM $Fe(CN)_6^{4-}$ or 0.1 M PBS are performed and the current signals recorded. The electrodes are a modified gold electrode, acidified manganese dioxide/gold electrode, or graphene oxide/sodium alginate/acidified manganese dioxide/gold electrode. The electrochemical method includes cyclic voltammetry and differential pulse voltammetry (circular voltammetry conditions: scanning range: −0.2 to 0.6 V, amplitude: 0.05 V; differential pulse voltammetry conditions: scanning range: −0.2 to 0.6 V, amplitude: 0.05 V).

Figure 2:
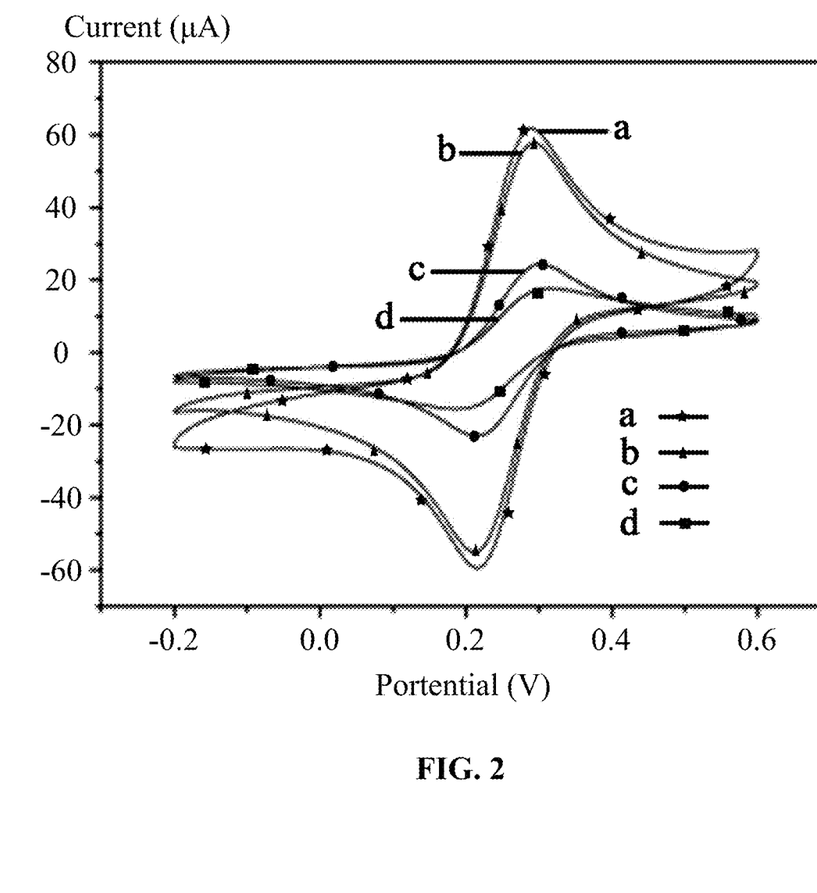
FIG. 2 is a cyclic voltammogram of a modified gold electrode according to one embodiment of the disclosure.
Figure 3:
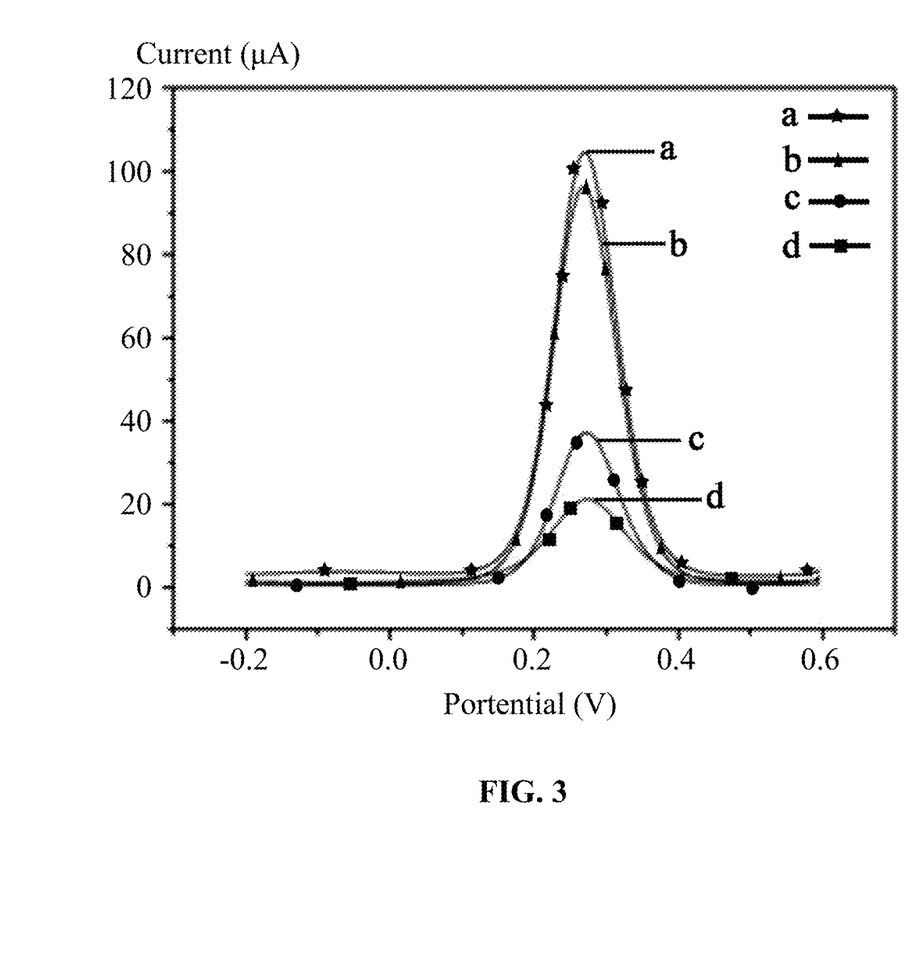
FIG. 3 is a differential pulse voltammogram of a modified gold electrode according to one embodiment of the disclosure.
Figure 4:
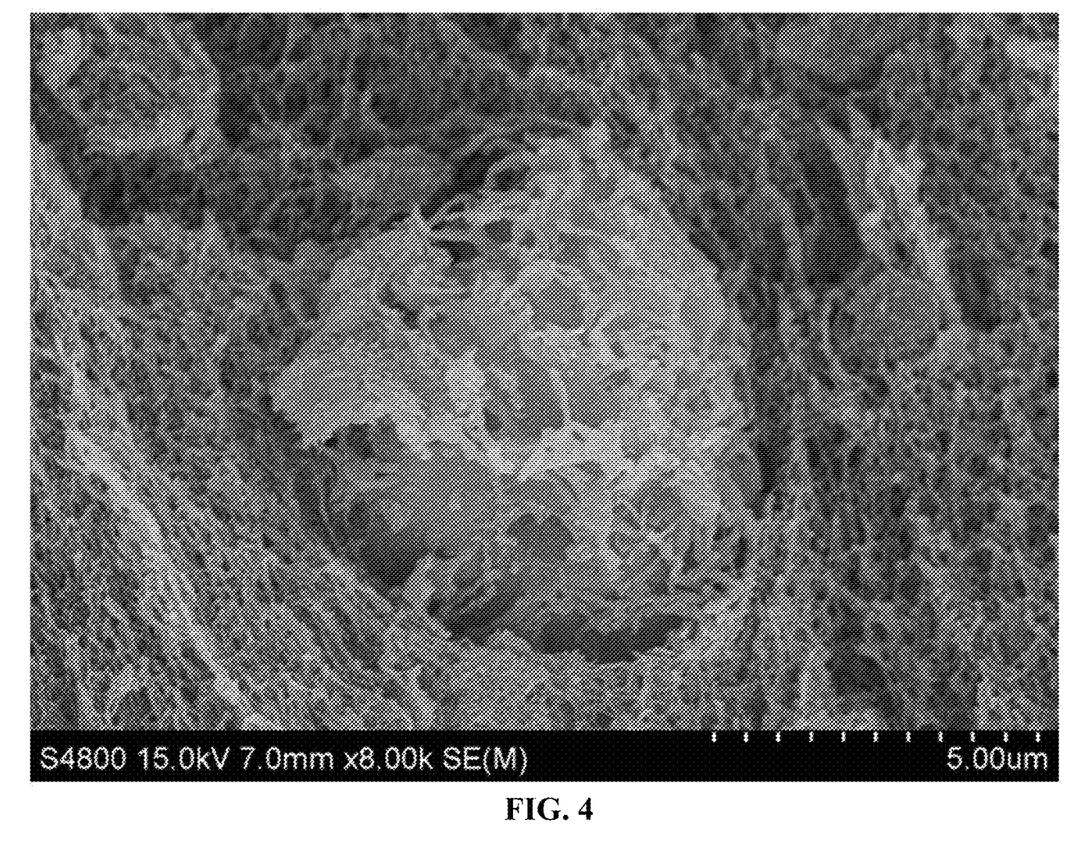
FIG. 4 is a scanning electron micrograph (SEM) of cells on the surface of a biosensor according to one embodiment of the disclosure.

FIGS. 2 and 3 show the modification results of the electrodes. FIG. 4 shows the gel/cell 3D structure under scanning electron microscopy.

In the following examples, the differential pulse voltammetry is selected as the electrochemical experiment method.

The following are examples to evaluate the antioxidant capacity of each substance using the biosensor of the disclosure.

EXAMPLE 1

Control Group

Positive control: a first biosensor was immersed in Tyrode's buffer at 37° C. (preparation of Tyrode's solution: 1000 mL Tyrode's solution: NaCl 8.0 g, 10% KCl 2.0 mL (0.2 g), 10% $MgSO_4.7H_2O$ 2.6 mL (0.26 g), 5% $NaH_2PO_4.2H_2O$ 1.3 mL (0.065 g), $NaHCO_3$ 1.0 g, 1 M $CaCl_2$ 1.8 mL (0.2 g), glucose 1.0 g), and PMA was then added to a concentration of 100 ng/mL. 10 min later, the first biosensor was washed with PBS buffer for 3 times (phosphate buffered saline) at pH=7.4, and then was connected to the electrochemical workstation. The first biosensor was electrochemically detected in a solution containing 1.0 mM $Fe(CN)_6^{3-}$, and the current signal was recorded and the peak current was read as $I_0$=84.6 μA.

Blank control: a third biosensor was immersed in Tyrode's buffer at 37° C. After standing for 10 min, the third biosensor was washed with PBS buffer for 3 times, and then was connected to an electrochemical workstation. The first biosensor was electrochemically detected in a solution containing 1.0 mM $Fe(CN)_6^{3-}$, and the current signal was recorded and the peak current was read as I=21.5 μA.

EXAMPLE 2

Evaluation of Antioxidant Capacity of Lactobacillus plantarum NJAU-01

1) Preparation of bacterial suspension: Lactobacillus plantarum NJAU-01 was used as the starter culture for inoculating fermented sausages, which was identified by API 50 CHL kit (bioMérieux Inc., France) and 16S rDNA sequencing analysis. The Lactobacillus plantarum NJAU-01 strain was grown in MRS broth for 18 h at 37° C. First, after harvesting, the bacterial cells were washed and resuspended in deionized water, and the cell concentration was adjusted to $10^5$, $10^6$, $10^7$, $10^8$, $10^9$ and $10^{10}$ CFU/mL. Next, the cells were incubated with 1 mg/ml lysozyme at 37° C. for 30 min and then sonicated in an ice bath. After removal of cell debris by centrifugation (8000 g, 10 min, 4° C.), the supernatant was obtained bacterial suspension of Lactobacillus plantarum NJAU-01.

Figure 5:
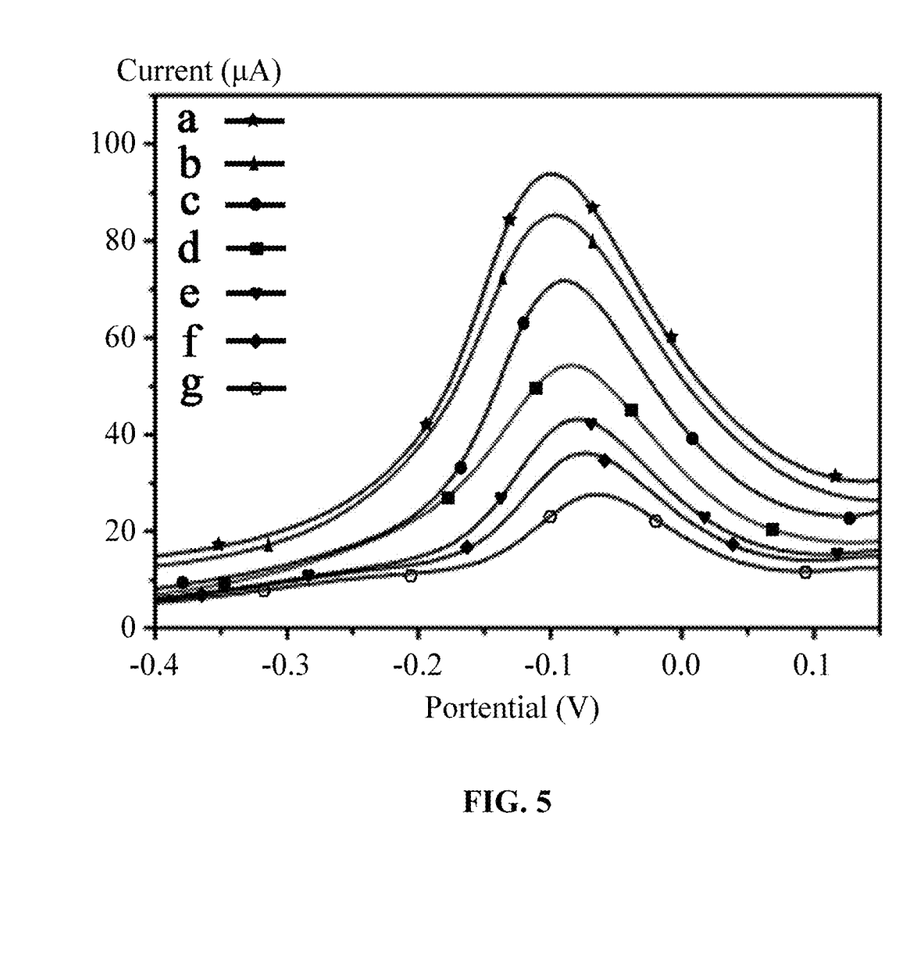
FIG. 5 is a differential pulse voltammogram of Lactobacillus plantarum NJAU-01 at different concentrations.
Figure 6:
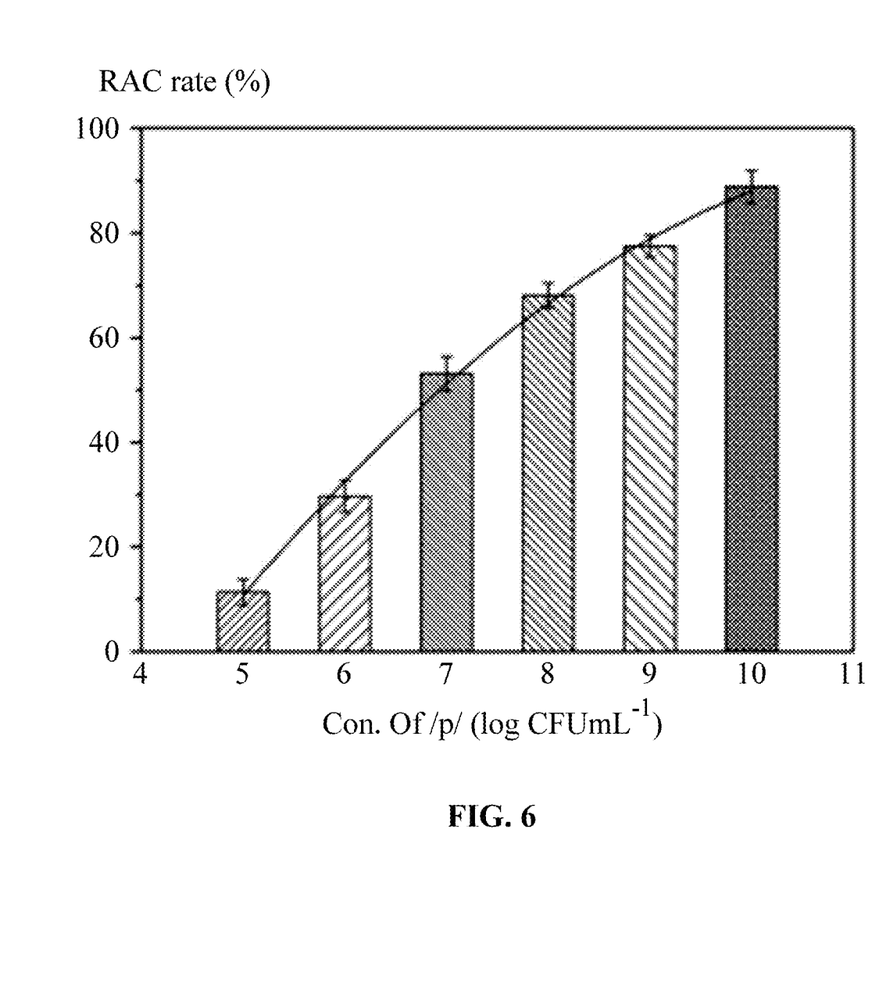
FIG. 6 is a graph of relative antioxidant capacity of Lactobacillus plantarum NJAU-01.

2) Pretreatment: the bacterial suspension of Lactobacillus plantarum NJAU-01 and a second biosensor were placed in Tyrode's buffer at 37° C., and PMA was then added to a concentration of 100 ng/mL. After standing for 10 min, the second biosensor were washed with PBS buffer for 3 times, and the biosensor was connected to the electrochemical workstation;

3) Electrochemical experiment: the second biosensor was used for electrochemical experiment in a PBS solution containing 1.0 mM $Fe(CN)_6^{3-}$. Subsequently, the current signal and the peak current $l_{s1}$ were recorded and read, respectively. And its relative antioxidant value $RAC_1$ was calculated, as shown in Table 1 and FIGS. 5 and 6.

TABLE 1

Evaluation of antioxidant capacity of Lactobacillus plantarum NJAU-01

| | Peak current $I_{s1}$ (μA) | $RAC_1$ (%) |
|---|---|---|
| $10^5$ CFU/mL | 74.0 | 16.8 |
| $10^6$ CFU/mL | 66.0 | 29.5 |
| $10^7$ CFU/mL | 51.2 | 53.1 |
| $10^8$ CFU/mL | 41.8 | 68.0 |
| $10^9$ CFU/mL | 36.2 | 76.8 |
| $10^{10}$ CFU/mL | 28.5 | 88.9 |

Table 1 shows that the peak current decreases significantly with the increase of the concentration of Lactobacillus plantarum NJAU-01, demonstrating that the high concentration of Lactobacillus plantarum strain exhibits good antioxidant capacity.

EXAMPLE 3

Evaluation of Antioxidant Capacity of Tea Polyphenols

1) Preparation of tea polyphenol solution: tea polyphenol was accurately weighed for 1.20 g and dissolved in 200 mL of absolute ethanol to prepare a tea polyphenol solution having a concentration of 0.6%.

2) Pretreatment: the tea polyphenol solution and the biosensor IV were immersed in Tyrode's buffer at 37° C., and PMA was then added to a concentration of 100 ng/mL. After standing for 10 min, the biosensor IV was washed with PBS buffer for 3 times, and was then connected to an electrochemical workstation.

Figure 7:
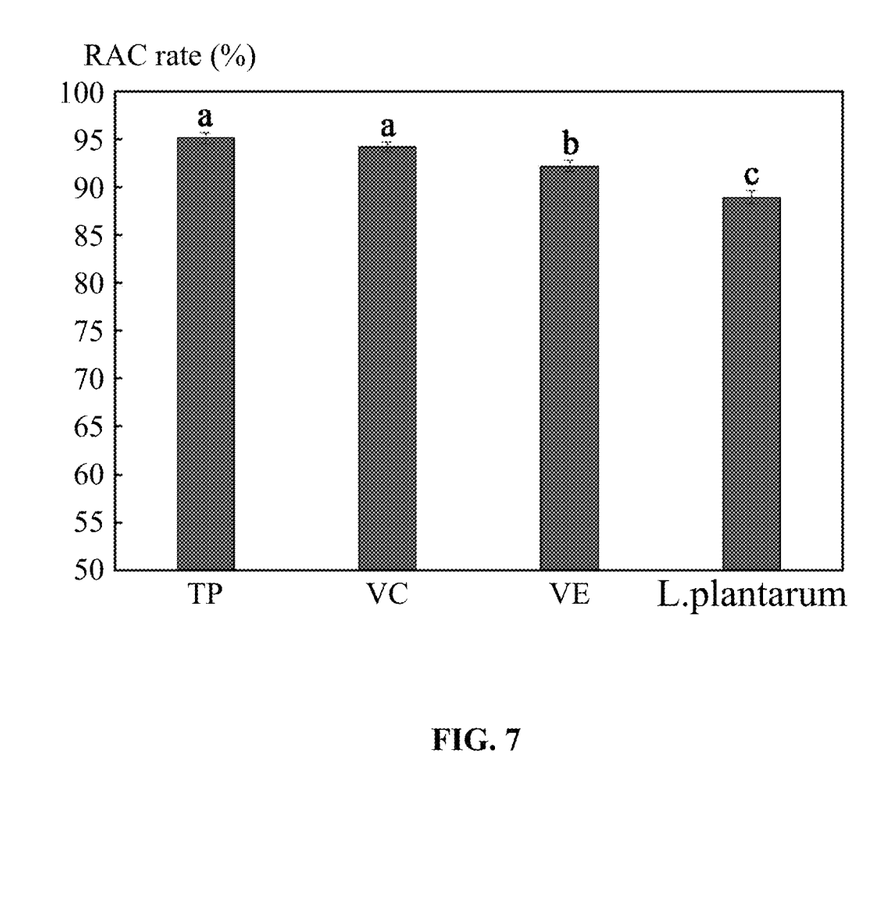
FIG. 7 shows RAC values of tea polyphenols, vitamin C, vitamin E and $10^{10}$ CFU/mL of Lactobacillus plantarum NJAU-01.

3) Electrochemical experiment: the biosensor IV was used for electrochemical experiment in a solution containing 1.0 mM $Fe(CN)_6^{4-}$. Subsequently, the current signal was recorded and the peak current $I_{s2}$ was read, where $I_{s2}$=24.7 μA. And relative antioxidant value (RAC2) of tea polyphenol was 95.1%, as shown in FIG. 7.

EXAMPLE 4

Evaluation of Antioxidant Capacity of Vitamin E

1) Preparation of $V_E$ solution: $V_E$ was accurately weighed for 1.20 g and dissolved in 200 mL of absolute ethanol to prepare a VE solution with a concentration of 0.6%.

2) Pretreatment: the $V_E$ solution and the biosensor were immersed in Tyrode's buffer at 37° C., and PMA was then added to a concentration of 100 ng/mL. After standing for 10 min, the biosensor was washed with PBS buffer for 3 times, and was then connected to an electrochemical workstation.

3) Electrochemical experiment: the biosensor was used for electrochemical experiment in a solution containing 0.1 M (mol/L) PBS. Subsequently, the current signal was recorded and the peak current $I_{s3}$ was read, where $I_{s3}$=26.5 µA. And relative antioxidant value (RAC3) of VE was 92.2%, as shown in FIG. 7.

EXAMPLE 5

Evaluation of Antioxidant Capacity of Vitamin C

1) Preparation of $V_C$ solution: $V_C$ was accurately weighed for 1.20 g and dissolved in 200 mL of absolute ethanol to prepare a $V_C$ solution with a concentration of 0.6%.

2) Pretreatment: the $V_C$ solution and the biosensor were immersed in Tyrode's buffer at 37° C., and PMA was then added to a concentration of 100 ng/mL. After standing for 10 min, the biosensor was washed with PBS buffer for 3 times, and was then connected to an electrochemical workstation.

3) Electrochemical experiment: the biosensor was used for electrochemical experiment in a solution containing 0.1 M (mol/L) PBS. Subsequently, the current signal was recorded and the peak current $I_{s4}$ was read, where $I_{s4}$=25.3 µA. And relative antioxidant value (RAC4) of VE was 94.2%, as shown in FIG. 7.

FIG. 7 shows that tea polyphenols, $V_C$, $V_E$ and Lactobacillus plantarum NJAU-01 have strong antioxidant capacity, and the antioxidant capacity of each antioxidant was as follow: tea polyphenols>$V_C$>$V_E$>Lactobacillus plantarum NJAU-01.

The experimental method of the disclosure is simple and time-saving, and the antioxidant capacity of each antioxidant substance can be visually compared according to the result.

It will be obvious to those skilled in the art that changes and modifications may be made, and therefore, the aim in the appended claims is to cover all such changes and modifications.

What is claimed is:

1. A method of preparing a biosensor, the biosensor comprising a modified gold electrode, and macrophages RAW264.7 immobilized on the modified gold electrode, the method comprising:
    a) dissolving manganese dioxide ($MnO_2$) in a mixed acid of concentrated $H_2SO_4$ and concentrated $HNO_3$ in an ultrasonic bath to obtain a mixed solution, stirring the mixed solution in an ice bath for 3-5 hrs, centrifuging the mixed solution, washing a resulting product with water and drying to obtain an acidified $MnO_2$ nanomaterial;
    b) dispersing the acidified $MnO_2$ nanomaterial in a chitosan solution in the presence of ultrasonic wave to obtain a suspension having a solid phase concentration of 0.9-1.1 mg/mL, taking 8-12 µL of the suspension and adding dropwise to a surface of a dried gold electrode, drying at 4-6° C., to yield a modified electrode;
    c) mixing graphene oxide and Dulbecco's Modified Eagle Medium (DMEM) having a concentration of 10 mmol/L according to a mass/volume ratio of 0.1 g/100 mL, sonicating for 4-6 min to yield a graphene oxide mixed solution, dropwise adding the graphene oxide mixed solution to a DMEM containing 1% sodium alginate, to yield a mixed gel of sodium alginate and graphene oxide, wherein the added graphene oxide mixed solution accounts for 10 wt. % of the DMEM containing 1% sodium alginate;
    d) culturing the macrophages RAW264.7 in DMEM containing 10% (v/v) fetal bovine serum (FBS) at 37° C. in the presence of 5% (v/v) $CO_2$ for 2-3 days, to obtain a macrophage suspension;
    e) mixing the macrophage suspension and the mixed gel of sodium alginate and graphene oxide in a volume ratio of 1: 1, taking 4-6 µL of a resulting mixture and adding to a surface of the modified electrode; immersing the modified electrode with the macrophages on it in a $CaCl_2$ solution for 3-5 min, and placing the $CaCl_2$ solution with the modified electrode in it in an incubator having 5% (v/v) $CO_2$ at 37° C. for 2-4 min, to yield a biosensor.

2. The method of claim 1, wherein the method further comprises:
    immersing the biosensor prepared in e) in Piranha solution comprising sulfuric acid and 30% hydrogen peroxide with a volume ratio of 7: 3 for 12-18 min;
    polishing the surface of the modified electrode with $Al_2O_3$ polishing powders having particle sizes of 0.3 µm and 0.05 µm, respectively; ultrasonically washing the biosensor with 5% dilute sulfuric acid, absolute ethanol and water in sequence for 5-8 min, respectively, drying under a nitrogen atmosphere, and storing at 4° C.

3. The method of claim 1, wherein a volume ratio of the concentrated $H_2SO_4$ to the concentrated $HNO_3$ in a) is 3: 1.

4. A method for evaluating antioxidant capacity of a test sample using at least three biosensors, each of the biosensor comprising a modified gold electrode, and macrophages RAW264.7 immobilized on the modified gold electrode, the method comprising:
    1) immersing a first biosensor in a Tyrode's buffer at 37° C., adding propylene glycol monomethyl ether acetate (PMA) to the Tyrode's buffer until the PMA concentration reaches 100 ng/mL, 10 min later, washing a the first biosensor with PBS buffer 2-4 times, and connecting the first biosensor to a first electrochemical workstation;
    2) immersing a second biosensor in Tyrode's buffer at 37° C., adding the test sample and PMA to the Tyrode's buffer until the final PMA concentration reaches 100 ng/mL, 10 min later, washing the second biosensor with PBS buffer 2-4 times, and connecting the second biosensor to a second electrochemical workstation;
    3) conducting differential pulse voltammetry (DPV) assays with the first biosensor and the second biosensor in a solution 1.0 mM $Fe(CN)_6^{3-}$, 1.0 mM $Fe(CN)_6^{4-}$ or 0.1 M PBS, recording current signals, reading peak currents and marking as $I_0$ and $I_s$, respectively, wherein $I_0$ is the peak current obtained by using the first biosensor and in the presense of 100 ng/mL PMA and $I_s$ is the peak current obtained by using the second biosensor and in the presence of the test sample;
    4) determining whether the test sample has antioxidant capacity:
        4. 1) $I_0$>$I_s$ indicates that the test sample has an antioxidant capacity, and proceeding to 5); and
        4.2) $I_0$<$I_s$ indicates that the test sample has no antioxidant capacity; and
    5) calculating a relative antioxidant capacity (RAC) value to evaluate the antioxidant capacity of the test sample, wherein the RAC value is calculated through the following equation:

$$RAC = \frac{(I_0 - I_s)}{(I_0 - I)} \times 100\%$$

and I is the peak current obtained by using a third biosensor and in the absense of PMA.

5. The method of claim 4, wherein the PBS buffer in 1) has a pH value of 7.4.

6. The method of claim 4, wherein the DPV assays are conducted under conditions of: scanning range: −0.2 to 0.6 V, amplitude: 0.05 V.

7. The method of claim 4, wherein the antioxidant capacity of the test sample in 5) is evaluated as follows:
   a value of RAC greater than 10% and less than 40% indicates that the test sample has weak antioxidant capacity;
   a value of RAC between 40% and 70% indicates that the test sample has moderate antioxidant capacity; and
   a value of RAC greater than 70% indicates that the test sample has strong antioxidant capacity.

8. The method of claim 4, wherein the peak current I is measured as follows:
   immersing the third biosensor in Tyrode's buffer at 37° C. for 10 min, washing the third biosensor with PBS buffer for 3 times, connecting the third biosensor to a third electrochemical workstation, and conducting a DPV assay with the third biosensor in a solution containing 1.0 mM $Fe(CN)_6^{3-}$, 1.0 mM $Fe(CN)_6^{4-}$ or 0.1 M PBS, recording a current signal, reading a peak current and marking it as I.

\* \* \* \* \*